United States Patent
Lee et al.

(10) Patent No.: US 12,390,529 B2
(45) Date of Patent: Aug. 19, 2025

(54) STABLE INFUSION SOLUTION COMPOSITION CONTAINING SUGAR AND AMINO ACID

(71) Applicants: Geon Moo Lee, Gwangju (KR); In Seong Lee, Gwangju (KR); Jun Seong Lee, Gwangju (KR); Mi Boon Chung, Seoul (KR)

(72) Inventors: Geon Moo Lee, Gwangju (KR); In Seong Lee, Gwangju (KR); Jun Seong Lee, Gwangju (KR); Mi Boon Chung, Seoul (KR)

( * ) Notice: Subject to any disclaimer, the term of this patent is extended or adjusted under 35 U.S.C. 154(b) by 1004 days.

(21) Appl. No.: 17/265,858

(22) PCT Filed: Jul. 24, 2019

(86) PCT No.: PCT/KR2019/009200
§ 371 (c)(1),
(2) Date: Feb. 4, 2021

(87) PCT Pub. No.: WO2020/032439
PCT Pub. Date: Feb. 13, 2020

(65) Prior Publication Data
US 2021/0170030 A1    Jun. 10, 2021

(30) Foreign Application Priority Data
Aug. 6, 2018 (KR) .................. 10-2018-0091284

(51) Int. Cl.
A61K 47/26 (2006.01)
A61K 9/08 (2006.01)
A61K 47/18 (2017.01)
A61K 47/40 (2006.01)

(52) U.S. Cl.
CPC .............. *A61K 47/26* (2013.01); *A61K 9/08* (2013.01); *A61K 47/183* (2013.01); *A61K 47/40* (2013.01)

(58) Field of Classification Search
CPC ...... A23L 33/125; A23L 33/17; A23L 33/175; A61K 47/182; A61K 47/26; A61K 47/183; A61K 47/40; A61K 9/0029; A61K 9/08
See application file for complete search history.

(56) References Cited

U.S. PATENT DOCUMENTS

| | | | |
|---|---|---|---|
| 4,758,583 A * | 7/1988 | Cerami | A61K 8/40 |
| | | | 514/561 |
| 5,993,863 A | 11/1999 | Kikuchi et al. | |
| 9,572,885 B2 * | 2/2017 | Yum | A61K 47/14 |
| 2017/0121361 A1 | 5/2017 | Withers et al. | |
| 2020/0138839 A1 * | 5/2020 | Lee | A61K 31/7004 |

FOREIGN PATENT DOCUMENTS

| | | | | |
|---|---|---|---|---|
| AU | 47352 85 A | 4/1986 | | |
| EP | 0957692 B1 | 8/2003 | | |
| EP | 1172041 B1 | 12/2005 | | |
| EP | 3058833 A1 | 8/2016 | | |
| JP | 2006-509556 A | 3/2006 | | |
| KR | 10-2007-0100390 A | 10/2007 | | |
| KR | 10-2011-0131699 A | 12/2011 | | |
| KR | 10-2017-0111281 A | 10/2017 | | |
| KR | 10-2018-0105424 A | 9/2018 | | |
| WO | WO-2014151523 A1 * | 9/2014 | ........... | A23K 20/142 |
| WO | 2017/118994 A1 | 7/2017 | | |
| WO | WO-2018169274 A1 * | 9/2018 | ......... | A61K 31/7004 |

OTHER PUBLICATIONS

Written Opinion of the International Searching Authority from corresponding PCT Application No. PCT/KR2019/009200, dated Oct. 24, 2019.
International Search Report from corresponding PCT Application No. PCT/KR2019/009200, dated Oct. 24, 2019.
Bell, F. R., et al.; "The Effect of Duodenal Infusion of Milk, Casein, Lactose and Fat on Gastric Emptying and Acid Secretion in the Milk-Fed Calf", J. Physiol., 1978, 282, pp. 51-57.
Lee, M. H., et al.; "Recombinant Human Factor IX Produced from Transgenic Porcine Milk", Research Article, 2014, pp. 1-9.
Wu, G., et al.; "Free and Protein-Bound Amino Acids in Sow's Colostrum and Milk1,2", Nutrient Metabolism, 1994, pp. 415-424.
Extended European Search Report from corresponding EP Application No. 19846614.6, dated May 10, 2022.

* cited by examiner

*Primary Examiner* — Sarah Pihonak
(74) *Attorney, Agent, or Firm* — Harness, Dickey & Pierce, P.L.C.

(57) ABSTRACT

Disclosed is a stable mixture composition of an amino acid and a sugar, wherein the composition solves the problems of color change and stability reduction at the time of mixing of an amino acid and a sugar.

2 Claims, 6 Drawing Sheets

FIG. 1

| added stabilzer | Index | | |
|---|---|---|---|
| | linear equation (y = ax + b) | Osmolality var. rate per time (%/day) | time taken to change by 20% (day) |
| Control | y = 1.241x − 7.8017 | 1.2421 | 22.9 |
| β-Cyclodextrin | y = 0.8336x − 3.6317 | 0.8336 | 28.3 |
| Aminoguanidne | y = 0.8271x − 5.1133 | 0.8271 | 30.4 |

STABLE INFUSION SOLUTION COMPOSITION CONTAINING SUGAR AND AMINO ACID

CROSS-REFERENCE TO RELATED APPLICATIONS

This application is a national phase application of PCT Application No. PCT/KR2019/009200, filed on Jul. 24, 2019, which claims the benefit and priority to Korean Patent Application No. 10-2018-0091284, filed on Aug. 6, 2018. The entire disclosures of the applications identified in this paragraph are incorporated herein by references.

TECHNICAL FIELD

The present invention relates to a stable infusion composition comprising sugar and amino acid. If sugar and amino acid are mixed as components of an infusion composition, it has a defect that stability is decreased and discoloration occurs over time. The mixed solution composition of sugar and amino acid according to the present invention is invented to greatly reduce these disadvantages, to improve storage stability, and to enable simultaneous supply of sugar and amino acids which are essential nutrients for the human body.

BACKGROUND ART

Carbohydrates such as sugar have been found to play an important role in essential physiological functions of the human body such as immune system regulation, hormone secretion, and major signaling in the body as well as producing energy. Therefore, it is necessary to supply a specific sugar in order to maintain the health of the human body. In particular, since 8 kinds of sugars, i.e., glucose (Glu), galactose (Gal), mannose (Man), fucose (Fuc), xylose (Xy), N-Acetylglucosamine (GlcNAc), N-Acetylgalactosamine (GalNAc), N-Acetylneuraminic acid (NANA or sialic acid) play a very important role in maintaining physiological activity in the body, it is very important to supply them as needed for maintaining human health.

In addition, since amino acid generates energy as a raw material for muscle in the body and plays a role in helping the regeneration and recovery of human tissues by keeping metabolism smooth, it is essential to supply appropriate amino acids to maintain the health of the human body. Accordingly, in many cases, sugar and amino acids are required simultaneously for the prevention and treatment of diseases.

Therefore, a mixture of sugar and amino acids was attempted to be administered at the same time. However, due to the problem of browning reaction known as Maillard reaction, in the past, each of amino acid infusion solution and sugar infusion solution were mixed in the preparation process when using (i.e., prepared for use). But, this method has disadvantages that there is a concern of bacterial infection in the preparation process and that it takes a lot of time. In this point of view, if a mixed solution of sugar and amino acid with guaranteed stability can be supplied, it may be possible to efficiently provide patients with high-quality nutrient infusion therapy.

PRIOR ART DOCUMENT

Patent Document (Patent Document 1) Korean unexamined patent application publication No. 10-2011-0131699

SUMMARY

Technical Problem

The present invention is to solve the problem that stability is decreased and that discoloration occurs due to a reaction that occurs when sugar and amino acids are mixed, thereby providing a stable infusion solution composition of mixture of sugar and amino acid even though sugar and amino acid are mixed.

Technical Solution

In order to solve the above problems, the present inventors intended to prepare a stable mixed composition of sugar and amino acid with improved stability and effectiveness by discovering a stabilizer capable of suppressing the Maillard reaction between sugar and amino acid and enhancing the stability.

Advantageous Effects

The stable mixture composition of sugar and amino acid according to the present invention can solve the problems of discoloration and deterioration of stability that occur when sugar and amino acid are mixed, and it enables simultaneous supply of sugar and amino acid to efficiently provide essential nutrients of the human body.

In particular, generally, the infusion solution is not used immediately after manufacture, but is used while being stored in large quantities in a medical institution for a considerable period of time (generally, it is used while storing for 12 to 24 months in hospitals or clinics). Therefore, the storage stability is a very important factor to be considered in manufacturing the infusion solution.

Accordingly, the present inventors have studied to dramatically improve storage stability, and thus, it has become possible to prepare a stable mixed composition of sugar and amino acid.

DETAILED DESCRIPTION

The present invention relates to a stable mixture solution composition of sugar and amino acid.

It is possible to supply sugars and amino acid simultaneously by preparing a mixture that dramatically improves stability by combining a specific stabilizer with amino acid and 8 sugars that play an important role in various physiological functions of the human body and contribute to health promotion.

The mixture composition of the present invention is a nutrient infusion solution in the form of a mixture of amino acids and sugars. The infusion solution comprises one or more amino acids and 8 sugars of glucose, galactose, mannose, fucose, xylose, N-acetylglucosamine, N-acetylgalactosamine and N-acetylneuraminic acid.

The sugars mentioned above are the main sugar components that are indispensable for the synthesis of glycoproteins. It is known that sugar chains are attached to more than 50% of proteins, and that the characteristic functions of most of such proteins are expressed only when sugars of a specific structure are bound. In addition, the bound sugar chain also increases or suppresses the function of the protein itself, and thus plays a role in more finely controlling cell growth and immune function, etc.

For example, glucose (grape sugar) acts as a representative energy source in the body; galactose functions as a distinguishing factor between different species; and mannose has effects of blood sugar regulation, immunity and anti-inflammatory. Fucose attached to an antibody is known to plays a very important role in regulating the activity of Antibody Dependent Cellular Cytotoxicity (ADCC) and is known to play a key role in bone growth. Xylose acts as an antimicrobial, antibacterial and anticancer substance that inhibits pathogens from binding to cell membrane mucus; and N-acetylglucosamine helps cartilage regeneration. N-acetylgalactosamine functions to inhibit the growth of tumor cells, alleviate rheumatoid arthritis and inhibit aging; and N-acetylneuraminic acid plays a critical role in antiviral action and brain growth.

In addition, amino acids are used as raw materials for muscles in the body to generate energy and facilitate metabolism to help regeneration and recovery of human tissues. Therefore, by supplying the above-mentioned 8 sugars in a mixed form in an amino acid infusion solution, efficient nutrient infusion therapy is possible, and the immune system and health of the human body can be further improved.

However, it is very difficult to prepare an infusion solution comprising the eight sugars mentioned above together with amino acids. This is due to the problem of reaction between sugar and amino acid. Therefore, in the present invention, a stabilizing agent that suppresses the reaction between sugar and amino acid and improves stability was discovered in order to solve the problem that occurs when sugar and amino acid are mixed.

In the present invention, ethylenediamine tetra acetic acid (EDTA), sodium tripolyphosphate, L-aspartic acid, β-cyclodextrin, taurine, pyridoxamine and aminoguanidine were selected as candidate stabilizers to be added to the mixture of sugar and amino acid, and stability was tested.

According to the present invention, a stabilizer that allows stability to be maintained for a long time even though sugar and amino acid are mixed is discovered. In order to compare the stability, the inventors used a method of comparing the rate of change in osmolality versus a baseline value over time and a method of comparing the degree of discoloration by setting color scale from 0 to 5. These methods use the phenomenon that, when a stabilizing effect occurs by adding an appropriate stabilizer into a mixture of sugar and amino acid, the decomposition of the substance occurs less, and that, as a result, the osmolality change is less than that of the control group wherein a stabilizer is not added.

The degree of discoloration over time was significantly reduced in the sugar/amino acid mixture to which the stabilizer which was discovered by the present inventors was added, compared with a sugar/amino acid mixture wherein no stabilizer was add or other stabilizer was added. The osmolality change rate is also decreased considerably.

In the present invention, the amino acid may be one or more selected from among 20 amino acids that can constitute a protein.

EXAMPLE

Example 1

Hereinafter, the present invention will be described in detail with reference to examples to help understand the present invention. However, the following examples are merely to illustrate the present invention, but the scope of the present invention is not limited to the following examples. The examples of the present invention are provided to more completely explain the present invention to those skilled in the art.

Experimental Example 1. Preparation of a Mixed Composition of Sugar and Amino Acid Infusion Solution Comprising Different Candidate of Stabilizer Substances A. Materials and Devices Eight sugars of glucose, galactose, mannose, fucose, xylose, N-acetylglucosamine, N-acetylgalactosamine and N-acetylneuraminic acid obtained from Sigma-Aldrich (St. Louis, Missouri, USA) were used.

The above 8 sugars were dissolved in water for injection (JW Pharmaceutical Corp.), and then mixed with 89.4% Proamin injection (Hanall BioPharma) which is a commercially available amino acid injection solution to prepare a mixed composition of sugar and amino acid infusion solution. The Proamin injection contains amino acids such as isoleucine, leucine, lysine acetate, methionine, phenylalanine, threonine, tryptophan, valine, alanine, arginine, aspartic acid, cysteine, glutamic acid, histidine, proline, serine, tyrosine and glycine, etc.

In order to adjust the pH of the sample, 1N NaOH solution (Samchun Pure Chemical Co., Ltd.) was used. The pH of the infusion solutions containing eight sugars and amino acids was adjusted to about 6.0 using a pH meter (METTLER TOLEDO Seven Compact pH/Ion).

As stabilizer candidates to be added to the mixed composition of amino acids and sugars, 98.0% ethylenediaminetetraacetic acid disodium salt dihydrate (EDTA-2Na dihydrate, Daejung Chemical Co., Ltd.), 85.0% sodium tripolyphosphate (Sigma-Aldrich), L-Aspartic Acid (Sigma-Aldrich), 97% β-cyclodextrin (Sigma-Aldrich), 99% Taurine (Sigma-Aldrich), pyridoxamine (Sigma-Aldrich) and aminoguanidine (Sigma-Aldrich) were used.

After the addition of the stabilizer candidate material, the osmolality variation rate (%) versus the baseline value over time was measured and the degree of color change using a color scale was measured in order to evaluate the stabilization effect. The osmolality was measured using an osmotic pressure meter (OSMOMAT 030, Cryoscopic osmometer). The change of color was observed with naked eyes and indicated with a color scale of 0 to 5, wherein the number increases as browning deepens.

B. Experimental Method

As shown in Table 1 below, a mixed solution composition F1 of Proamin injection and eight sugars, and compositions F2, F3, F4, F5, F6, F7 and F8 to each of which a different stabilizer was added respectively were prepared. The specific experimental method is as follows:

First, 12.4 mg of each of 8 sugars was added to 20 mL of water for injection (therefore, the added total amount of the 8 sugars is 12.4 mg*8=99.2 mg), and then it was mixed with 20 mL of amino acid injection solution (Proamin injection), and sufficiently stirred. The stirred mixture was subdivided into 10 vials of 4 mL. Thereafter, different stabilizers were added to each vial and mixed well. The pH was adjusted to about 6.0 by adding an appropriate amount of 1N NaOH to each vial.

For accelerated reaction, F1, F2, F3, F4, F5, F6, F7, F8 vials are wrapped with parafilm to seal these vials, and accelerated tests are conducted under conditions of 40±2° C. temperature and 75±5% relative humidity. The osmolality was measured and the color change was observed.

Glucose, galactose, mannose, fucose, xylose, N-acetylglucosamine, N-acetylgalactosamine and N-acetylneuraminic acid of eight sugars are added in the amount of 12.4 mg, respectively. Therefore, the total amount of the eight sugars is 12.4 mg*8=99.4 mg.

C. Experiment Result

After the start of the accelerated test as a long-term storage stability test, discoloration began to appear after about 10 days in the control group F1 wherein no stabilizer is added. F3 comprising β-Cyclodextrin as a stabilizer and F6 comprising aminoguanidine as a stabilizer has less discoloration and lower osmolality variation rate (%) than F1. In the other samples except for F3 and F6, no significant results were obtained in color change and osmolality variation rate (%) compared to control group F1.

The experimental results are shown in Tables 2 and 3.

TABLE 2

Osmolality measurement result (unit: osmol/L) of sample F1, F2, F3, F4, F5, F6, F7, F8

| | | Osmolality (Relative variation rate (%) compared to the initial state) | | | |
|---|---|---|---|---|---|
| Formulation code | Preparation | After 7 days | After 14 days | After 21 days | After 28 days |
| F1(Control) | 0.598 | 0.619 (3.5%) | 0.656 (9.7%) | 0.706 (18.1%) | 0.760 (27.1%) |
| F2(Tripolyphosphate)* | 0.632 | | | | |
| F3(β-Cyclodextrin) | 0.591 | 0.609 (3.0%) | 0.643 (8.8%) | 0.694 (12.4%) | 0.706 (19.4%) |
| F4(Pyridoxamine)* | 0.648 | | | | |
| F5(Taurine)* | 0.625 | 0.650 (4.0%) | 0.706 (13.0%) | | |
| F6(Aminoguanidine) | 0.639 | 0.651 (1.9%) | 0.681 (6.6%) | 0.716 (12.0%) | 0.762 (19.2%) |
| F7(Aspartic acid) | 0.637 | 0.657 (3.1%) | 0.692 (8.6%) | 0.719 (12.9%) | 0.771 (21.0%) |
| F8(EDTA) | 0.616 | 0.636 (3.2%) | 0.687 (11.5%) | 0.717 (16.1%) | 0.765 (24.2%) |

*The measurement for the samples which shows greater change in osmolality and color change compared to control F1 was stopped hereafter.

Figure 1:
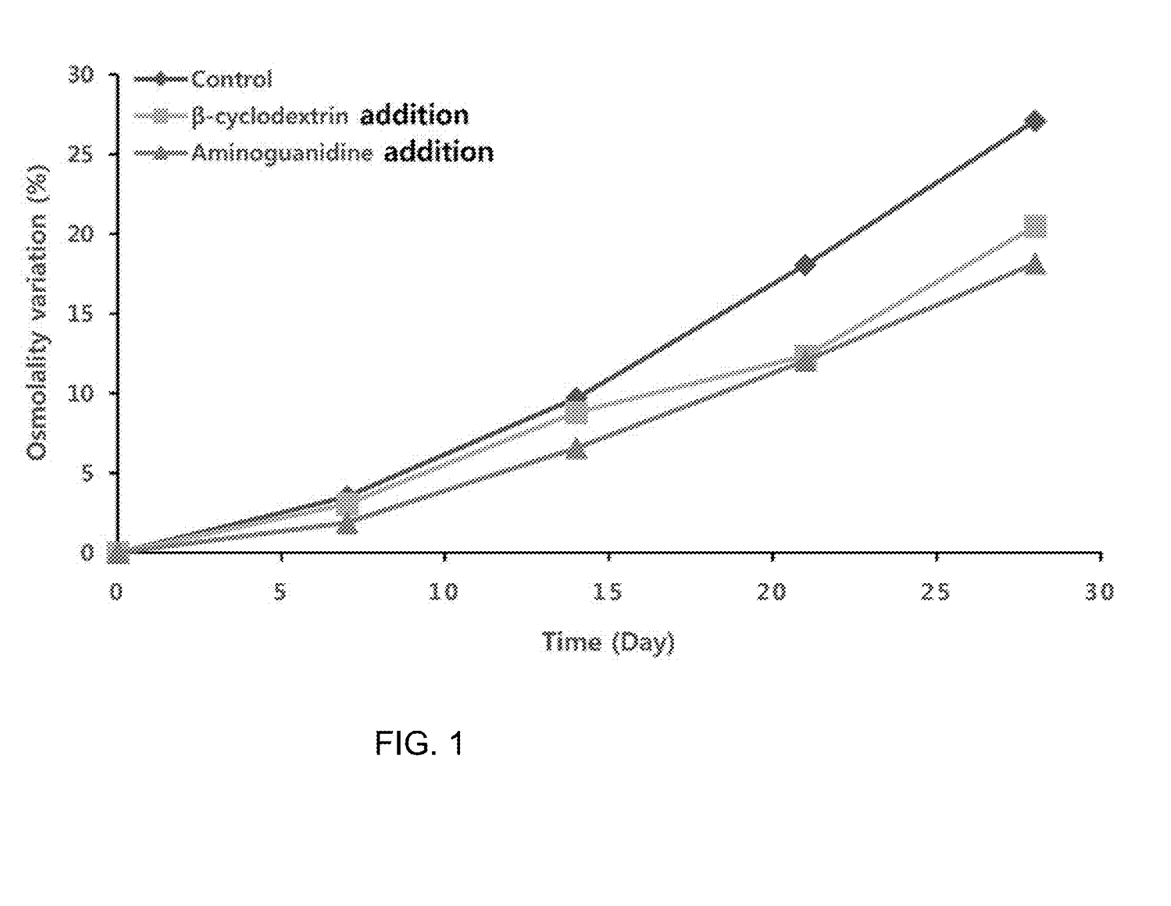
FIG. 1 is a comparison of the measured osmolality variation rate (%) of the mixture solution depending on the addition of different stabilizers from the candidate groups into the mixture solutions of 8 sugars and amino acids according to Experimental Example 1.
Figure 2:
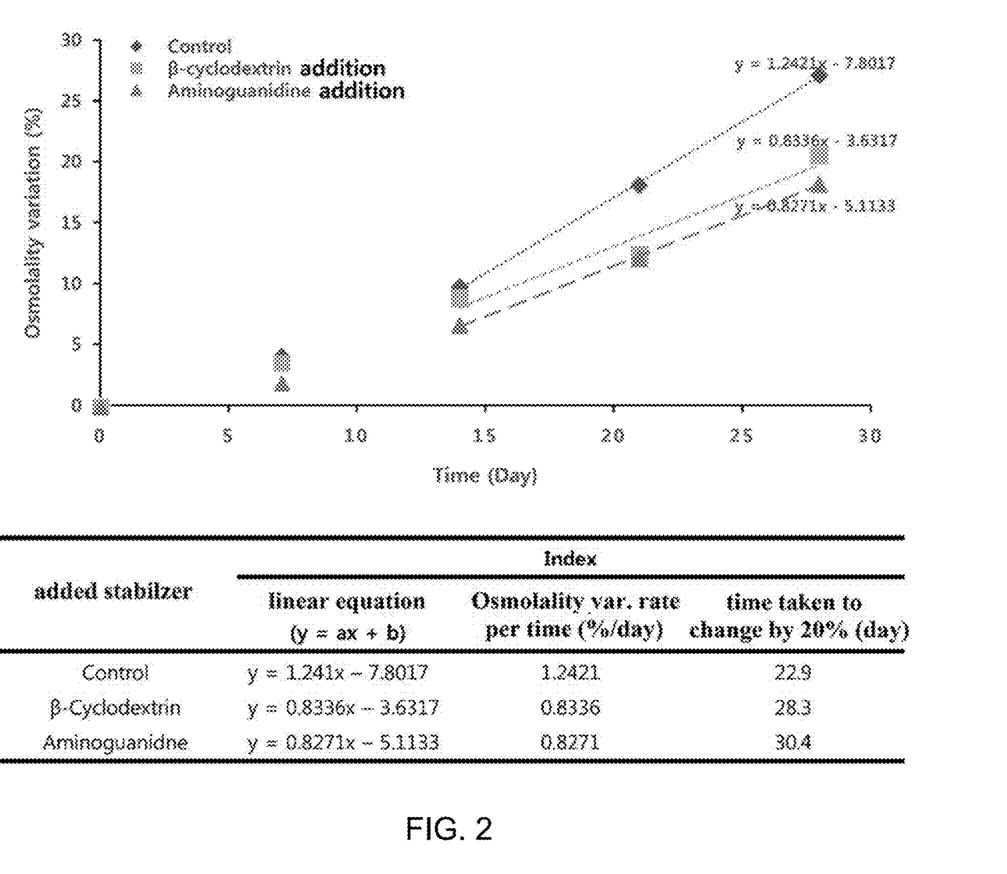
FIG. 2 shows the result of predicting time taken for the osmolality to change by 20% through linear regression analysis from the graph of the osmolality variation rate (%) of above FIG. 1.

FIG. 1 shows in graph the comparison of the osmolality variation rate (%) for F1, F3, and F6 in Table 2 above. FIG. 2 shows the result of predicting time taken for the osmolality to change by 20% through linear regression analysis from the graph of the osmolality variation rate (%) of above FIG. 1.

TABLE 1

Composition of the sample F1, F2, F3, F4, F5, F6, F7, F8

| | Formulation code | | | | | | | |
|---|---|---|---|---|---|---|---|---|
| Ingredients | F1 | F2 | F3 | F4 | F5 | F6 | F7 | F8 |
| Proamin (mL) | 2 | 2 | 2 | 2 | 2 | 2 | 2 | 2 |
| 8 sugars* (mg) | 12.4 | 12.4 | 12.4 | 12.4 | 12.4 | 12.4 | 12.4 | 12.4 |
| Water for injection (mL) | 2 | 2 | 2 | 2 | 2 | 2 | 2 | 2 |
| Tripolyphosphate (mg) | | 16 | | | | | | |
| β-Cyclodextrin (mg) | | | 16 | | | | | |
| Pyridoxamine (mg) | | | | 16 | | | | |
| Taurine (mg) | | | | | 16 | | | |
| Aminoguanidine (mg) | | | | | | 16 | | |
| Aspartic acid (mg) | | | | | | | 16 | |
| EDTA (mg) | | | | | | | | 16 |
| Total (mL) | 4 | 4 | 4 | 4 | 4 | 4 | 4 | 4 |

From FIG. 2 above, the stability is expected to be highest when aminoguanidine is used as a stabilizer.

TABLE 3

Color scale measurement result of sample F1, F2, F3, F4, F5, F6, F7, F8

| Formulation code | Color scale (0~5) | | | | |
|---|---|---|---|---|---|
| | Preparation | After 7 days | After 14 days | After 21 days | After 28 days |
| F1 (Control) | 0 | 0 | 2 | 3 | 4 |
| F2 (Tripolyphosphate) | 0 | 2 | 3 | 4 | 4 |
| F3 (β-Cyclodextrin) | 0 | 0 | 1 | 3 | 4 |
| F4 (Pyridoxamine) | 0 | 3 | 4 | 4 | 5 |
| F5 (Taurine) | 0 | 0 | 2 | 2 | 4 |
| F6 (Aminoguanidine) | 0 | 0 | 1 | 2 | 3 |
| F7 (Aspartic acid) | 0 | 0 | 2 | 3 | 4 |
| F8 (EDTA) | 0 | 0 | 2 | 3 | 4 |

Experimental Example 2. Preparation of a Mixed Composition of Sugar and Amino Acid Infusion Solution Comprising β-Cyclodextrin and Aminoguanidine, which Showed a Stabilizing Effect in Experimental Example 1, in Different Ratios A. Materials and Devices Eight sugars of glucose, galactose, mannose, fucose, xylose, N-acetylglucosamine, N-acetylgalactosamine and N-acetylneuraminic acid obtained from Sigma-Aldrich (St. Louis, Missouri, USA) were used.

The above 8 sugars were dissolved in water for injection (JW Pharmaceutical Corp.), and then mixed with 89.4% Proamin injection (Hanall BioPharma) which is a commercially available amino acid injection solution to prepare a mixed composition of sugar and amino acid infusion solution.

In order to adjust the pH of the sample, 1N NaOH solution (Samchun Pure Chemical Co., Ltd.) was used. The pH of the infusion solutions containing eight sugars and amino acids was adjusted to about 6.0 using a pH meter (METTLER TOLEDO Seven Compact pH/Ion).

As stabilizer, 97% β-cyclodextrin (Sigma-Aldrich) and aminoguanidine (Sigma-Aldrich) were used.

After the addition of the stabilizer, the osmolality variation rate (%) versus the baseline value over time was measured and the degree of color change using a color scale was measured in order to evaluate the stabilization effect. The osmolality was measured using an osmotic pressure meter (OSMOMAT 030, Cryoscopic osmometer). The change of color was observed with naked eyes and indicated with a color scale of 0 to 5, wherein the number increases as browning deepens.

B. Experimental Method

As shown in Table 4 below, compositions G1, G2, G3, G4, G5, G6 and G7 which comprise β-cyclodextrin and aminoguanidine, which showed a stabilizing effect in Experimental Example 1, in different ratios in a mixture of Proamin injection and 8 sugars were prepared, respectively. The specific experimental method is as follows:

First, 12.4 mg of each of 8 sugars was added to 20 mL of water for injection (therefore, the total amount of the added 8 sugars is 12.4 mg*8=99.2 mg), and then it was mixed with 20 mL of amino acid injection solution (Proamin injection), and sufficiently stirred. The stirred mixture was subdivided into 10 vials of 4 mL. Thereafter, β-cyclodextrin and/or aminoguanidine were added to each vial and mixed well. The pH was adjusted to about 6.0 by adding an appropriate amount of 1N NaOH to each vial.

For accelerated reaction, G1, G2, G3, G4, G5, G6, G7 vials are wrapped with parafilm to seal these vials, and accelerated tests are conducted under conditions of 40±2° C. temperature and 75±5% relative humidity. The osmolality was measured and the color change was observed.

TABLE 4

Composition of the sample G1, G2, G3, G4, G5, G6, G7

| Ingredients | Formulation code | | | | | | |
|---|---|---|---|---|---|---|---|
| | G1 | G2 | G3 | G4 | G5 | G6 | G7 |
| Proamin (mL) | 2 | 2 | 2 | 2 | 2 | 2 | 2 |
| 8 sugars * (mg) | 12.4 | 12.4 | 12.4 | 12.4 | 12.4 | 12.4 | 12.4 |
| Water for injection (mL) | 2 | 2 | 2 | 2 | 2 | 2 | 2 |
| β-cyclodextrin (mg) | 16 | | 16 | 16 | 16 | 8 | 32 |
| Aminoguanidine (mg) | | 16 | 8 | 16 | 32 | 16 | 16 |
| Total (mL) | 4 | 4 | 4 | 4 | 4 | 4 | 4 |

* Glucose, galactose, mannose, fucose, xylose, N-acetylglucosamine, N-acetylgalactosamine and N-acetylneuraminic acid of eight sugars are added in the amount of 12.4 mg, respectively. Therefore, the total amount of the eight sugars is 12.4 mg * 8 = 99.4 mg.

C. Experiment Result

After the start of the accelerated test as a long-term storage stability test, G3 comprising only aminoguanidine as a stabilizer has less discoloration and lower osmolality variation rate (%) than G2 comprising only β-Cyclodextrin as a stabilizer.

As for G3, G4 and G5 wherein β-cyclodextrin was mixed with aminoguanidine and wherein the amount of β-cyclodextrin was fixed and the amount of aminoguanidine was varied, the discoloration is less and the osmolality variation rate (%) is lower as the amount of aminoguanidine increased. On the other hand, as for G4, G6 and G7 wherein β-cyclodextrin was mixed with aminoguanidine and wherein the amount of aminoguanidine was fixed and the amount of β-cyclodextrin was varied, no significant results were obtained depending on the amount of β-cyclodextrin.

Therefore, it can be noticed that the effect of the stabilizer added to the mixture composition of the amino acid infusion solution and sugar was more influenced by aminoguanidine than by β-cyclodextrin.

The experimental results are shown in Tables 5 and 6.

TABLE 5

Osmolality measurement result (unit: osmol/L) of the sample G1, G2, G3, G4, G5, G6, G7

| Formulation code | Osmolality (Relative variation rate (%) compared to the initial state) | | | | |
|---|---|---|---|---|---|
| | Preparation | After 3 days | After 7 days | After 10 days | After 14 days |
| G1 (β-CD only) | 0.575 | 0.596 (3.6%) | 0.620 (7.8%) | 0.656 (14.1%) | 0.744 (31.7%) |
| G2 (AG only) | 0.630 | 0.643 (2.1%) | 0.656 (4.1%) | 0.705 (11.9%) | 0.800 (27.0%) |
| G3 (β-CD:AG = 16:8) | 0.602 | 0.613 (1.8%) | 0.628 (4.3%) | 0.683 (13.4%) | 0.782 (29.9%) |
| G4 (β-CD:AG = 16:16) | 0.628 | 0.630 (0.3%) | 0.652 (3.8%) | 0.702 (11.8%) | 0.747 (18.9%) |
| G5 (β-CD:AG = 16:32) | 0.685 | 0.687 (0.3%) | 0.708 (3.4%) | 0.757 (10.5%) | 0.787 (14.9%) |
| G6 (AG:β-CD = 16:8) | 0.628 | 0.631 (0.5%) | 0.652 (3.8%) | 0.720 (14.6%) | 0.803 (27.9%) |

TABLE 5-continued

Osmolality measurement result (unit: osmol/L)
of the sample G1, G2, G3, G4, G5, G6, G7

| Formulation code | Osmolality (Relative variation rate (%) compared to the initial state) | | | | |
|---|---|---|---|---|---|
| | Preparation | After 3 days | After 7 days | After 10 days | After 14 days |
| G7 (AG:β-CD = 16:32) | 0.637 | 0.639 (0.3%) | 0.647 (1.6%) | 0.721 (13.2%) | 0.810 (27.2%) |

β-CD = β-Cyclodextrin,
AG = Aminoguanidine

Figure 3:
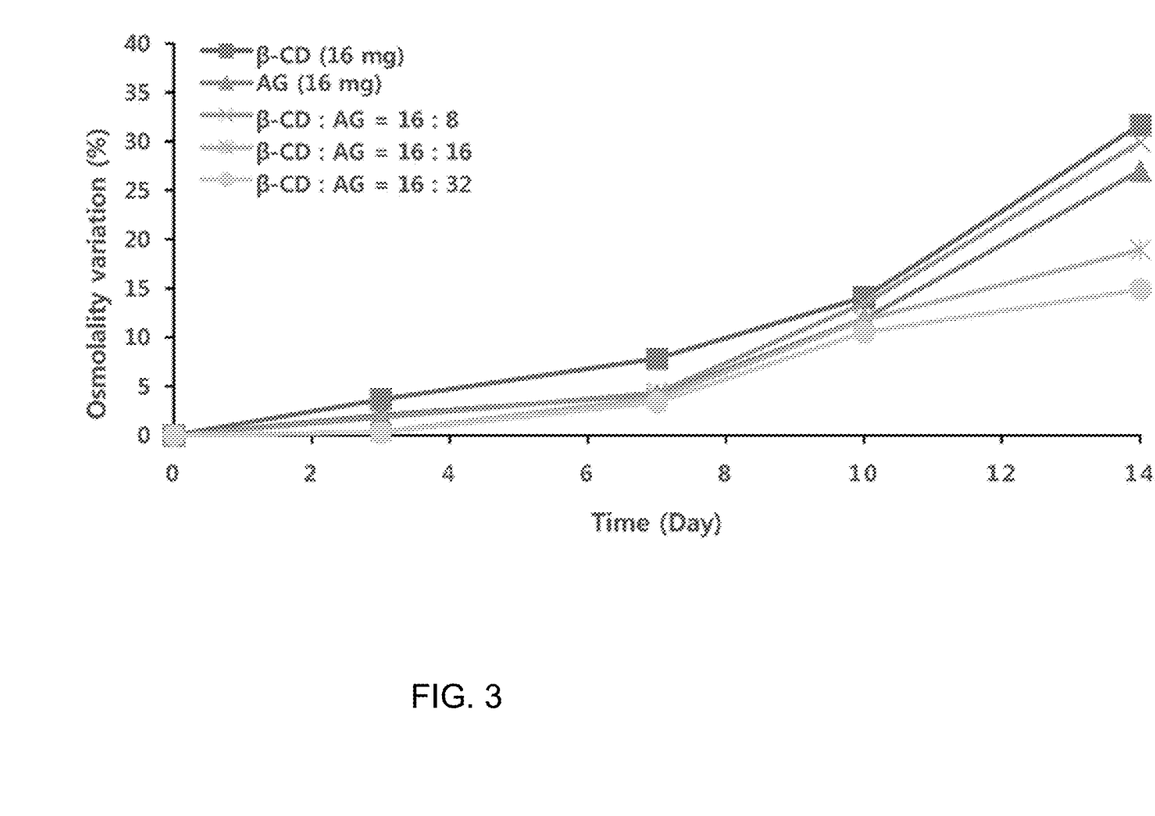
FIG. 3 is a comparison of the osmolality variation rate (%) of the mixture solution depending on the addition of mixture of beta-cyclodextrin and aminoguanidine with various ratios, which stabilizers were found to have a stabilizing effect in Experimental Example 1, into the mixture solution of 8 sugars and amino acids according to Experimental Example 2.
Figure 4:
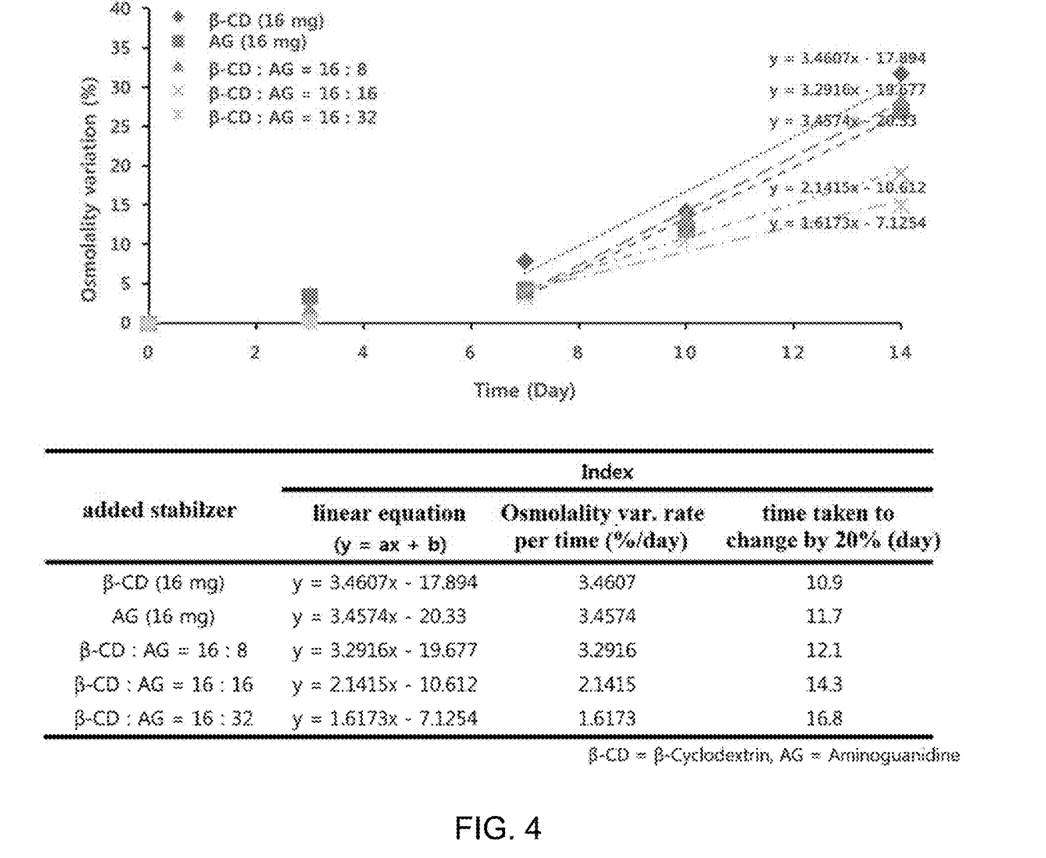
FIG. 4 shows the results of predicting time taken for the osmolality to change by 20% through linear regression analysis from the graph of the osmolality variation rate (%) of above FIG. 3.

FIG. 3 shows in graph the comparison of the osmolality variation rate (%) for G1 to G5 in Table 5 above. FIG. 4 shows the result of predicting time taken for the osmolality to change by 20% through linear regression analysis from the graph of the osmolality variation rate (%) of above FIG. 3.

From FIG. 4 above, it can be seen that the stabilization effect is higher when β-cyclodextrin and aminoguanidine are mixed and used as stabilizer rather than β-cyclodextrin or aminoguanidine are used alone. In addition, it can be seen that the stabilization effect is higher when the amount of aminoguanidine is greater than that of β-cyclodextrin.

TABLE 6

Color scale measurement result of the
sample G1, G2, G3, G4, G5, G6, G7

| Formulation code | Color scale (0~5) | | | | |
|---|---|---|---|---|---|
| | Preparation | After 3 days | After 7 days | After 10 days | After 14 days |
| G1 (β-CD only) | 0 | 0 | 1 | 1 | 4 |
| G2 (AG only) | 0 | 0 | 0 | 1 | 3 |
| G3 (β-CD:AG = 16:8) | 0 | 0 | 0 | 1 | 4 |
| G4 (β-CD:AG = 16:16) | 0 | 0 | 0 | 1 | 2 |
| G5 (β-CD:AG = 16:32) | 0 | 0 | 0 | 0 | 2 |
| G6 (AG:β-CD = 16:8) | 0 | 0 | 0 | 1 | 3 |
| G7 (AG:β-CD = 16:32) | 0 | 0 | 0 | 1 | 2 |

β-CD = β-Cyclodextrin,
AG = Aminoguanidine

Experimental Example 3. Preparation of a Mixed Composition of Sugar and Amino Acid Infusion Solution Comprising Aminoguanidine, which Showed a Higher Stabilizing Effect in Experimental Example 2, in Different Amounts A. Materials and Devices Eight sugars of glucose, galactose, mannose, fucose, xylose, N-acetylglucosamine, N-acetylgalactosamine and N-acetylneuraminic acid obtained from Sigma-Aldrich (St. Louis, Missouri, USA) were used.

The above 8 sugars were dissolved in water for injection (JW Pharmaceutical Corp.), and then mixed with 89.4% Proamin injection (Hanall BioPharma) which is a commercially available amino acid injection solution to prepare a mixed composition of sugar and amino acid infusion solution.

In order to adjust the pH of the sample, 1N NaOH solution (Samchun Pure Chemical Co., Ltd.) was used. The pH of the infusion solutions containing eight sugars and amino acids was adjusted to about 6.0 using a pH meter (METTLER TOLEDO Seven Compact pH/Ion).

As stabilizer, aminoguanidine (Sigma-Aldrich) were used.

After the addition of the stabilizer, the osmolality variation rate (%) versus the baseline value over time was measured and the degree of color change using a color scale was measured in order to evaluate the stabilization effect. The osmolality was measured using an osmotic pressure meter (OSMOMAT 030, Cryoscopic osmometer). The change of color was observed with naked eyes and indicated with a color scale of 0 to 5, wherein the number increases as browning deepens.

B. Experimental Method

As shown in Table 7 below, compositions H1, H2, H3 and H4 which comprise aminoguanidine, which showed higher stabilizing effect in Experimental Example 2, in different amounts in a mixture of Proamin injection and 8 sugars were prepared, respectively. The specific experimental method is as follows:

First, 62 mg of each of 8 sugars was added to 10 mL of water for injection (therefore, the added total amount of the 8 sugars is 62 mg*8=496 mg), and then it was mixed with 10 mL of amino acid injection solution (Proamin injection), and sufficiently stirred. The stirred mixture was subdivided into 5 vials of 4 mL. Thereafter, aminoguanidine was added to each vial in the amount shown in Table 7 and mixed well. The pH was adjusted to about 6.0 by adding an appropriate amount of 1N NaOH to each vial.

For accelerated reaction, H1, H2, H3, H4 vials are wrapped with parafilm to seal these vials, and accelerated tests are conducted under conditions of 40±2° C. temperature and 75±5% relative humidity. The osmolality was measured and the color change was observed.

TABLE 7

Composition of the sample H1, H2, H3, H4

| Ingredients | Formulation code | | | |
|---|---|---|---|---|
| | H1 | H2 | H3 | H4 |
| Proamin (mL) | 2 | 2 | 2 | 2 |
| 8 sugars * (mg) | 12.4 | 12.4 | 12.4 | 12.4 |
| Water for injection (mL) | 2 | 2 | 2 | 2 |
| Aminoguanidine (mg) | 0.1 | 1 | 10 | 100 |
| Total (mL) | 4 | 4 | 4 | 4 |

* Glucose, galactose, mannose, fucose, xylose, N-acetylglucosamine, N-acetylgalactosamine and N-acetylneuraminic acid of eight sugars are added in the amount of 12.4 mg, respectively. Therefore, the total amount of the eight sugars is 12.4 mg * 8 = 99.2 mg.

C. Experiment Result

After the start of the accelerated test as a long-term storage stability test, discoloration began to appear after about 14 days. H1, H2, H3, and H4 containing 0.1 mg, 1 mg, 10 mg and 100 mg of aminoguanidine as a stabilizer, respectively, has less discoloration and lower osmolality variation rate (%) on the whole. Such effect is more increased as the amount of added aminoguanidine is increased.

Accordingly, it was found that the stabilizing effect of the mixed composition of amino acids and sugars was largely influenced by aminoguanidine, and that the stabilizing effect was also increased as the amount of added aminoguanidine is increased.

The experimental results are shown in Tables 8 and 9.

TABLE 8

Osmolality measurement result (unit: osmol/L) of sample H1, H2, H3, H4

Osmolality (Relative variation rate (%) compared to the initial state)

| Formulation code | Preparation | After 4 days | After 7 days | After 10 days | After 14 days | After 18 days |
|---|---|---|---|---|---|---|
| H1 | 0.590 | 0.618 (4.7%) | 0.624 (5.8%) | 0.637 (8.0%) | 0.658 (11.5%) | 0.685 (16.1%) |
| H2 | 0.591 | 0.603 (2.0%) | 0.614 (3.9%) | 0.629 (6.4%) | 0.642 (8.6%) | 0.667 (12.8%) |
| H3 | 0.624 | 0.639 (2.4%) | 0.646 (3.5%) | 0.660 (5.8%) | 0.673 (7.8%) | 0.688 (10.2%) |
| H4 | 0.906 | 0.908 (0.2%) | 0.916 (1.1%) | 0.923 (1.9%) | 0.937 (3.4%) | 0.956 (5.5%) |

Figure 5:
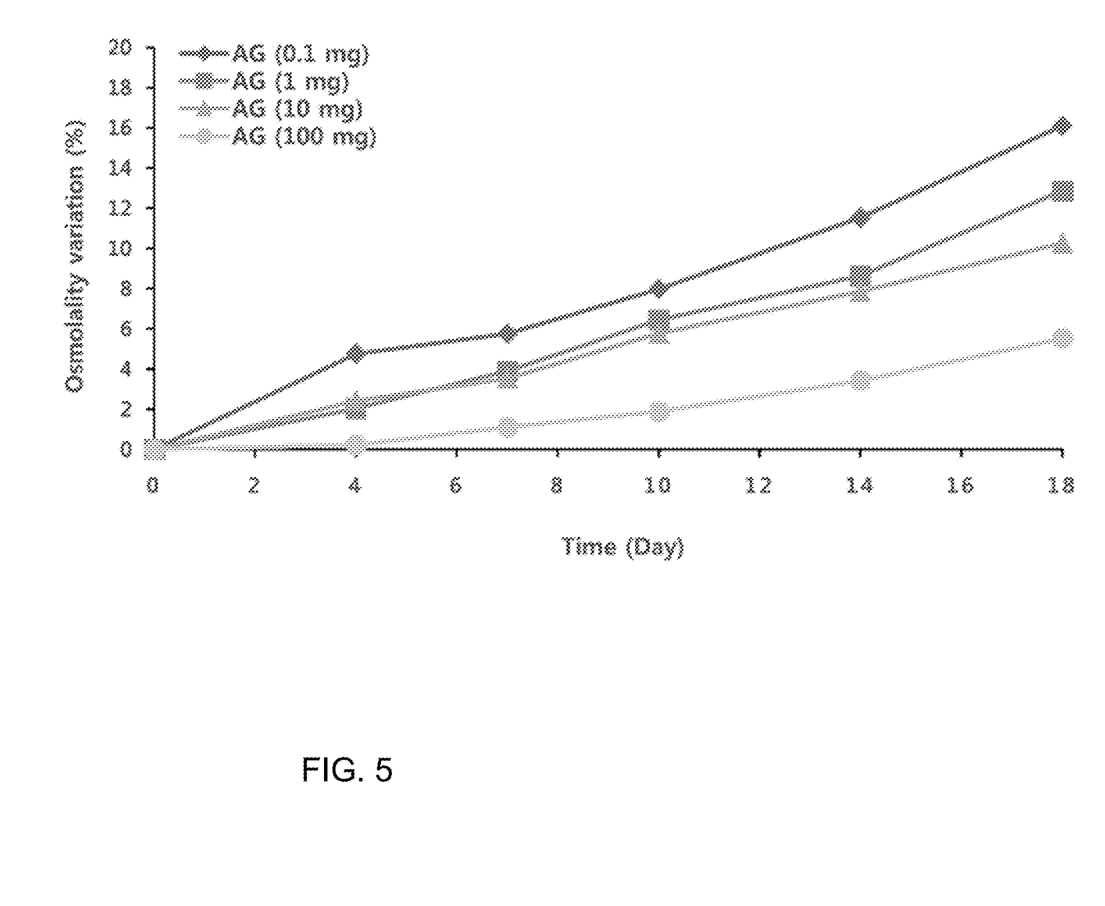
FIG. 5 is a comparison of the osmolality variation rate (%) of the mixture solution depending on addition of aminoguanidine in various amount, which stabilizer was found to have a greater stabilizing effect in Experimental Example 2, into the mixture solution of 8 sugars and amino acids according to Experimental Example 3.
Figure 6:
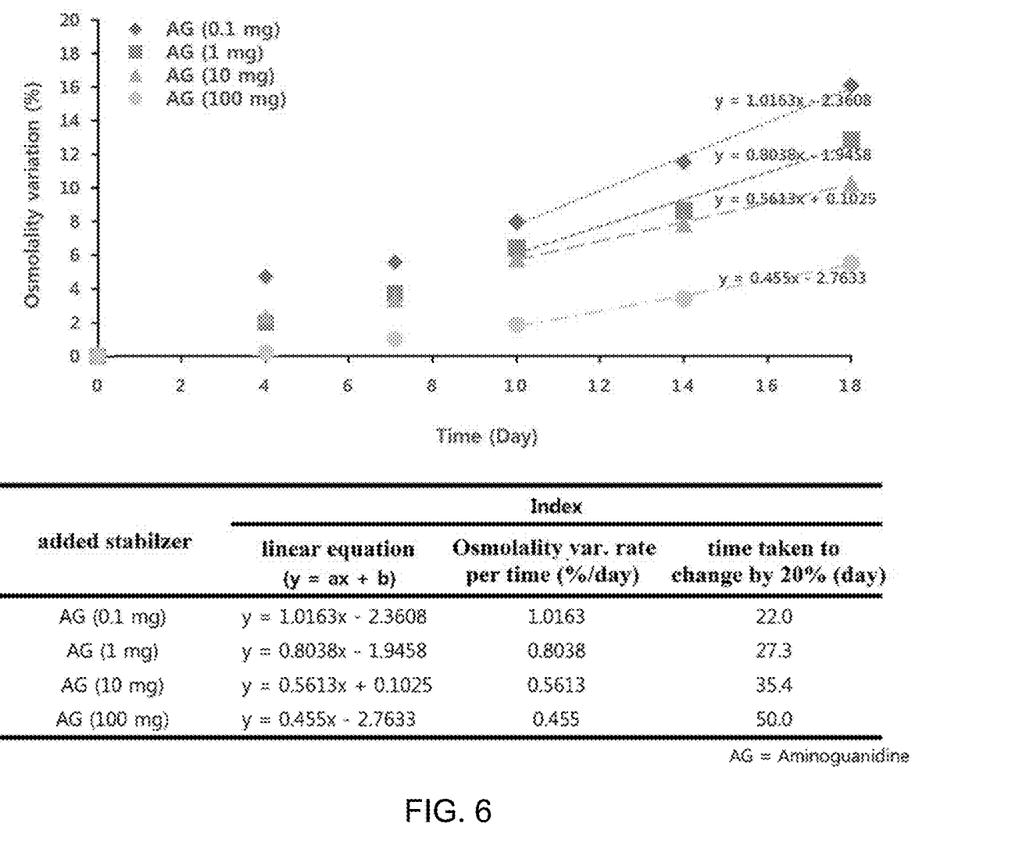
FIG. 6 shows the results of predicting time taken for the osmolality to change by 20% through linear regression analysis from the graph of the osmolality variation rate (%) of above FIG. 5.

FIG. 5 shows in graph the comparison of the osmolality variation rate (%) for H1 to H4 in Table 8 above. FIG. 6 shows the result of predicting time taken for the osmolality to change by 20% through linear regression analysis from the graph of the osmolality variation rate (%) of above FIG. 5.

From FIG. 6 above, it can be expected that the stabilizing effect is also increased as the amount of added aminoguanidine is increased.

TABLE 9

Color scale measurement result of the sample H1, H2, H3, H4

Color scale (0~5)

| Formulation code | Produce | After 4 days | After 7 days | After 10 days | After 14 days | After 18 days |
|---|---|---|---|---|---|---|
| H1 | 0 | 0 | 0 | 0 | 2 | 3 |
| H2 | 0 | 0 | 0 | 0 | 1 | 3 |
| H3 | 0 | 0 | 0 | 0 | 0 | 1 |
| H4 | 0 | 0 | 0 | 0 | 0 | 0 |

INDUSTRIAL AVAILABILITY

The stable mixed infusion solution composition of sugar and amino acid according to the present invention greatly improved stability, especially long-term storage stability.

What is claimed is:

1. An Infusion solution composition comprising:
   one or more amino acids selected from the group consisting of 20 amino acids capable of constituting a protein;
   glucose, galactose, mannose, fucose, xylose, N-acetylglucosamine, N-acetylgalactosamine and N-acetylneuraminic acid; and
   a stabilizer,
   wherein the stabilizer is one or more selected from the group consisting of β-cyclodextrin and aminoguanidine.

2. An Infusion solution composition comprising:
   one or more amino acids selected from the group consisting of 20 amino acids capable of constituting a protein;
   glucose, galactose, mannose, fucose, xylose, N-acetylglucosamine, N-acetylgalactosamine and N-acetylneuraminic acid; and
   a stabilizer,
   wherein the stabilizer is aminoguanidine.

* * * * *